(12) United States Patent
Madabhushi et al.

(10) Patent No.: US 11,107,583 B2
(45) Date of Patent: Aug. 31, 2021

(54) SEQUENTIAL INTEGRATION OF ADVERSARIAL NETWORKS WITH HANDCRAFTED FEATURES (SANWICH): IDENTIFYING SITES OF PROGNOSTIC SIGNIFICANCE FOR PREDICTING CANCER RECURRENCE

(71) Applicant: Case Western Reserve University, Cleveland, OH (US)

(72) Inventors: Anant Madabhushi, Shaker Heights, OH (US); Xiangxue Wang, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 222 days.

(21) Appl. No.: 16/359,214

(22) Filed: Mar. 20, 2019

(65) Prior Publication Data
US 2019/0295721 A1    Sep. 26, 2019

Related U.S. Application Data

(60) Provisional application No. 62/645,339, filed on Mar. 20, 2018.

(51) Int. Cl.
| | | |
|---|---|---|
| *G16H 50/20* | (2018.01) | |
| *G16H 30/20* | (2018.01) | |
| *G06N 5/04* | (2006.01) | |
| *G06N 20/00* | (2019.01) | |
| *G06N 3/08* | (2006.01) | |
| *G06T 7/00* | (2017.01) | |

(52) U.S. Cl.
CPC ............ *G16H 50/20* (2018.01); *G06N 3/08* (2013.01); *G06N 5/046* (2013.01); *G06N 20/00* (2019.01); *G06T 7/0012* (2013.01); *G16H 30/20* (2018.01)

(58) Field of Classification Search
CPC .............................. G16H 50/20; G16H 30/20
See application file for complete search history.

(56) References Cited

PUBLICATIONS

Wang et al. "Prediction of Recurrence in Early Stage Non-Small Cell Lung Cancer Using Computer Extracted Nuclear eatures From Digital H&E Images." Scientific Reports—7: 13543—DOI:10.1038/s41598-017-13773-7. Published on Oct. 19, 2017.

*Primary Examiner* — Tuan H Nguyen
(74) *Attorney, Agent, or Firm* — Eschweiler & Potashnik, LLC (57) ABSTRACT

Embodiments discussed herein facilitate generation of a prognosis for a medical condition based on determination of one or more histomorphometric features for tiles of a whole slide image (WSI) that have been identified as the most prognostically significant tiles of the WSI. A first set of embodiments discussed herein relates to training of a fully convolutional network (FCN) to determine the prognostic significance of pixels of a WSI. A second set of embodiments discussed herein relates to determination of a prognosis based on analysis of regions identified as the most prognostically significant by a trained FCN.

18 Claims, 9 Drawing Sheets

SEQUENTIAL INTEGRATION OF ADVERSARIAL NETWORKS WITH HANDCRAFTED FEATURES (SANWICH): IDENTIFYING SITES OF PROGNOSTIC SIGNIFICANCE FOR PREDICTING CANCER RECURRENCE

CROSS REFERENCE TO RELATED APPLICATIONS

This application claims the benefit of U.S. Provisional Patent Application No. 62/645,339 filed Mar. 20, 2018, entitled "SEQUENTIAL INTEGRATION OF ADVERSARIAL NETWORKS WITH HANDCRAFTED FEATURES (SANWICH): IDENTIFYING SITES OF PROGNOSTIC SIGNIFICANCE FOR PREDICTING LUNG CANCER RECURRENCE", the contents of which are herein incorporated by reference in their entirety.

BACKGROUND

Recent advances in whole slide image (WSI) tissue scanner and digital image analysis have enabled the development of machine based image classifiers for disease detection, diagnosis, prognosis and pre-diction of treatment response. Typically, the machine based approaches for prognosis prediction rely on either tissue punches (Tissue Microarrays (TMAs)) or small regions randomly extracted from larger whole slide images. Unfortunately, neither one of these approaches is able to account for intra-tumoral heterogeneity and may not even reflect the most prognostic regions within the tumor.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Various embodiments can employ techniques discussed herein for sequential integration of adversarial networks with handcrafted features (referred to herein as "SANwicH") to identify regions within a WSI (Whole Slide Image) that are more representative of disease prognosis. The sequential approach discussed herein and employed by various embodiments can leverage the power of adversarial convolutional neural network (CNN) to help identify candidate regions from WSIs from which to subsequently extract histomorphometric features (e.g., nuclear shape, texture, etc.) to predict outcome. Unlike existing techniques, this integration of CNNs and handcrafted features can thereby provide a focused, intuitive predictor of disease outcome from stained (e.g., H&E (hematoxylin and eosin) stained) tissue slide images. In an example implementation, on a cohort of 50 WSIs from patients with early stage non-small cell lung cancer (NSCLC), an embodiment employing SANwicH techniques yielded an AUC (Area Under the Curve) of a ROC (Receiver Operating Characteristic) curve) of 0.81, hazards ratio=7.3974, and p=0.002. Additionally, SANwicH techniques discuss herein were found to be superior when compared to corresponding handcrafted classifiers that employed randomly sampled image tiles and/or all tiles from the WSI.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

With the recent advances in digital pathology, a number of researchers have been developing machine vision based approaches for predicting disease presence, outcome and treatment response. While deep learning (DL)-based algorithms have also been widely employed for image classification and object recognition tasks, such as in macular degeneration and diabetic retinopathy, when it comes to a prognostic classifier, there tends to be a preference for more intuitive and interpretable hand-crafted features. For instance, one group has reported that nuclear shape, texture and spatial architectural features were significantly correlated with the risk of recurrence in early-stage non-small cell lung cancer (NSCLC). Another group has similarly shown that morphological features from stromal regions in H&E stained tissue images were associated with survival in breast cancer.

There has, however, been a recent surge in interest to identify possible ways to integrate DL and handcrafted feature based approaches in order to create more accurate, and interpretable, prediction models. One of the central questions of integrating handcrafted and DL approaches is with regard to the preferred strategy for combining the different feature representations. One group has employed a parallel integration approach to combine DL representations and handcrafted features for mitosis detection from whole slide breast cancer images. However, parallel integration approaches first involve generating dual representations across the entire landscape of the whole slide image (WSI) and then subsequently combining them. A first disadvantage of this approach is that, owing to the size of the WSI images (which could easily range from 2 Gb-10 Gb), this approach may not be computationally efficient. More importantly, in the context of building a prognostic model, the critical concern is in identifying the most relevant locations on whole slide images for subsequent feature interrogation and classifier construction. Given that most tumors have a substantial degree of intra-tumoral heterogeneity, it is certainly not obvious as to which parts of the tumor contain the most pertinent information to predict disease outcome for a specific patient. Consequently, the two major challenges in developing image based prognostic markers of disease outcome from WSIs are (a) automatically identifying the regions on WSI images that are most likely to harbor the prognostic information and (b) subsequently extracting the most predictive handcrafted features from within the prognostic targets to predict disease outcome.

A number of previous algorithms that have focused on predicting disease outcome have involved image analysis of tissue microarray (TMA) spots. These TMAs represent tissue punches derived from specific locations within the tumor block, but these locations are determined in an ad hoc fashion and hence may not capture the most aggressive or prognostic tumor loci. While some approaches have focused on random sampling of tumor tiles from WSIs, these approaches might again not capture the most representative prognostic locations, given the heterogeneity of the tumor microenvironment. Although one group has reported that the prediction accuracy tends to stabilize when more than 15 tiles were used per WSI, the choice of tile number is arbitrary. Moreover, random sampling invariably leads to signal averaging from across different parts of the tumor, thereby failing to address the issue of informed region identification from within the WSI.

Figure 1:
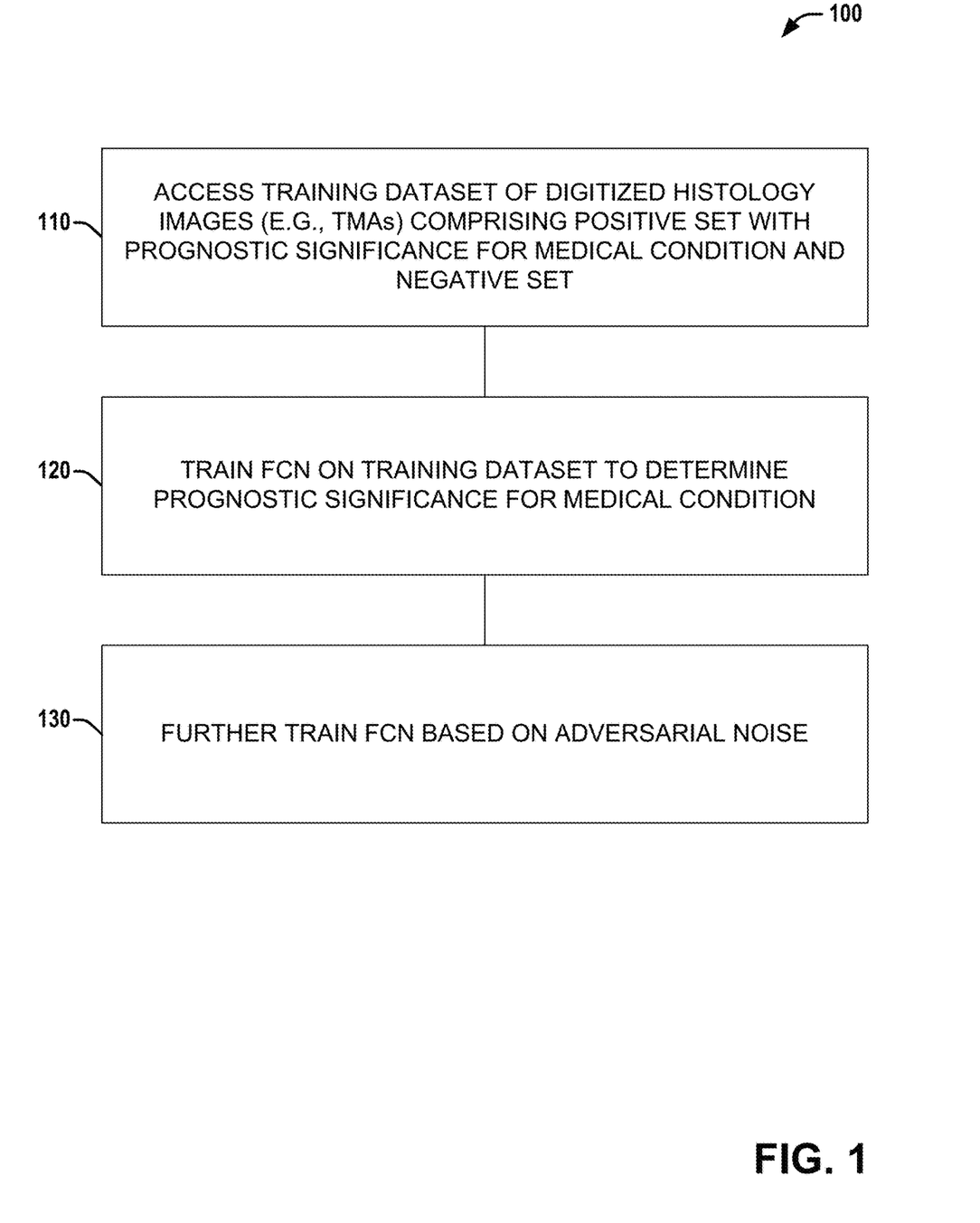
FIG. 1 illustrates a flow diagram of an example method or set of operations that employs sequential integration of adversarial networks with handcrafted features (SANwicH) techniques to build a prediction model for determining a prognosis associated with a medical condition, according to various embodiments discussed herein.

Various embodiments can employ techniques referred to herein as sequential integration of adversarial networks with handcrafted features (also referred to as SANwicH), comprising a framework (discussed in greater detail below) to sequentially combine fully convolutional adversarial networks with handcrafted nuclear features to generate prognoses based on stained (e.g., H&E stained) histological image data. Additionally, example embodiments are discussed below, applying the SANwicH techniques to the specific use case of predicting recurrence for early stage non-small-cell lung cancer (NSCLC), although in various embodiments, techniques described herein can be applied to generated prognoses for other medical conditions (e.g., other tumor types, etc.). Referring to FIG. 1, illustrated is a diagram showing an example flow of a method or set of operations 100 that employs sequential integration of adversarial networks with handcrafted features (SANwicH) techniques to build a prediction model for determining a prognosis associated with a medical condition, according to various embodiments discussed herein.

The set of operations 100 can comprise, at 110, accessing a training dataset of digitized images of stained (e.g., H&E stained) histology, for example, tissue microarrays (TMAs). Each image (e.g., digitized image of a TMA) can comprise a plurality of pixels, wherein each pixel can have an associated intensity. Various embodiments can be employed in different use cases associated with different medical conditions. The training dataset can comprise both a positive training set of digitized images (e.g., of TMAs) and a negative training set of digitized images (e.g., of TMAs) in connection with a given medical condition. The positive training set can comprise images that have histomorphometric features (e.g., one or more handcrafted features that have been determined to be prognostically significant specifically in connection with the given medical condition, etc.) that are predictive of an outcome (e.g., recurrence (at all, or early vs. late, etc.), non-recurrence, recurrence-free survival, progression-free survival, survival time, etc.) of the given medical condition (e.g., cancer such as early stage NSCLC, etc.). The negative training set can comprise images of samples that are irrelevant, have non-prognostic patterns (e.g., normal stromal tissue, etc.), have artifacts (e.g., folding, missing tissue, etc.), or are non-diagnostic tissue (e.g., frozen).

The histomorphometric features can comprise any of a variety of features, such as one or more of: (1) at least one global graph feature (e.g., wherein each nuclear centroid can be designated as a graph node, all the nodes in each digitized image or tile can be connected to construct a variety of global nuclear graphs, such that, depending on the type of connectivity between the nodes (e.g., Voronoi diagram, Delaunay triangulation, or minimum spanning tree, etc.), different global graphs can be constructed, and from each global graph, associated descriptors capturing the topology and spatial relation of nuclei can be employed); (2) at least one local nuclear cluster graph feature (e.g., wherein a cluster of nuclei can be identified, from which the centroid of the cluster can then be identified, with a cluster defined by a local aggregation of proximally located nuclei. Cluster centroids can be used to define the nodes of the cluster graph, and a similar set of topological and spatial relationship attributes to those of global graph features can be determined for each local cluster in the digitized image or tile); (3) at least one nuclei shape feature (e.g., nuclear shape features that can be extracted from the segmented boundary of each nucleus, for example, nuclear area, perimeter, min/max radius, Fourier transform of the nuclear contour, etc., wherein a mean, median, standard deviation, etc. can be determined for all the nuclei in the digitized image or tile); (4) at least one nuclei orientation entropy feature (the directionality of each nucleus can be determined by performing principal component analysis on the Cartesian coordinate locations on the set of boundary points of each nucleus, second order statistics can be calculated (e.g., contrast energy, entropy, etc.) on the orientation of all nuclei within local clusters, and the mean, median, and standard deviation measurements for each of these statistics can be aggregated across all the clusters in the digitized image or tile); and/or (5) at least one nuclei texture feature (e.g., Gray level co-occurrence features which capture second order joint intensity statistics can be employed to encode the textural heterogeneity of each nucleus, and for each feature, the corresponding mean and standard deviation values can be measured for each digitized image or tile). Handcrafted features can comprise one or more features as discussed above that that have been determined (e.g., via an algorithm such as minimum redundancy maximum relevance (mRMR) and/or QDA (Quadratic Discriminant Analysis), etc.) to be of high prognostic significance specifically in connection with the given medical condition (e.g., wherein the one or more handcrafted features comprise the one or more known features having the highest prognostic significance for the given medical condition). In one example embodiment related to determining recurrence or non-recurrence of early stage NSCLC, the set of handcrafted features can comprise one or more of: graph features such as a ratio of minimum and maximum area of polygons within a nuclear Voronoi graph and average number of nearest neighbors within a 40-pixel radius; shape features such as mean of Fourier shape descriptor 4 and min/max ratio of Fourier shape descriptor 8; and texture features such as Haralick descriptors comprising standard deviations of contrast variance, contrast energy, and contrast inverse moment.

The set of operations 100 can further comprise, at 120, training a fully convolutional network (FCN) based on the training set to identify regions of prognostic significance in digitized stained (e.g., H&E stained) histological images.

The set of operations 100 can further comprise, at 130, further training the FCN based on adversarial noise that maximizes the probability of false prediction, which can substantially improve the robustness and consistency of the predictions generated by the FCN.

Figure 2:
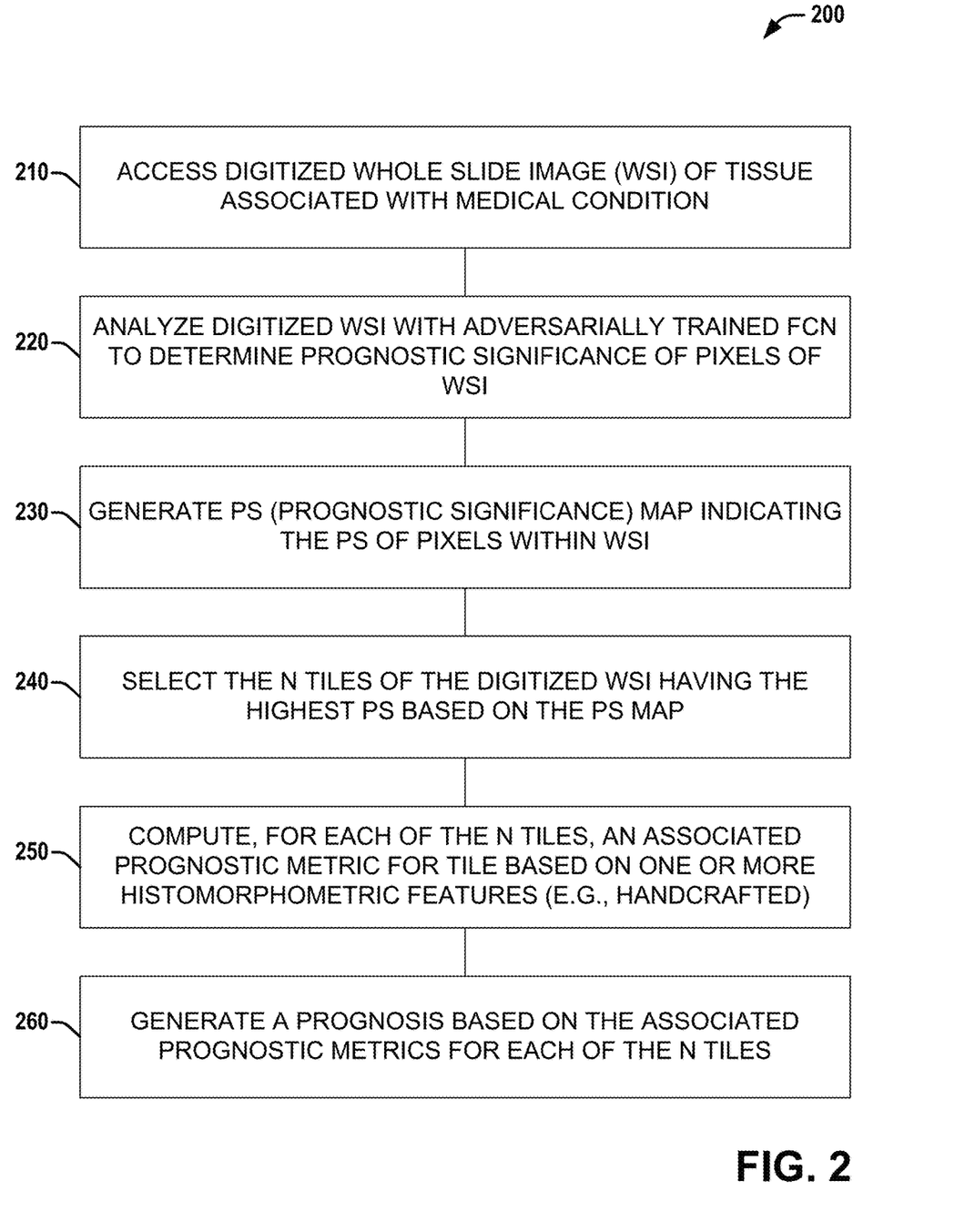
FIG. 2 illustrates a flow diagram of an example method or set of operations that employs a prediction model generated via sequential integration of adversarial networks with handcrafted features (SANwicH) techniques to generate a prognosis associated with a medical condition, according to various embodiments discussed herein.

Optionally, the FCN trained via set of operations 100 can be validated based on a test dataset with WSIs corresponding to known outcomes of the medical condition in a manner similar to set of operations 200 discussed below, with the additional operation of comparing the prognosis to the known outcome for each image of the test dataset. Based on validation, one or more parameters (e.g., tile size, number of tiles, etc.) can be adjusted to increase the accuracy of the trained FCN. Additionally, in various embodiments, the tile size can depend on properties of the digitized image (e.g., magnification, number of pixels, etc.).

Referring to FIG. 2, illustrated is a diagram showing an example flow of a method or set of operations 200 that employs a prediction model generated via sequential integration of adversarial networks with handcrafted features (SANwicH) techniques to generate a prognosis associated with a medical condition, according to various embodiments discussed herein.

The set of operations 200 can comprise, at 210, accessing a digitized WSI (Whole Slide Image) of tissue associated with a medical condition. The tissue can be, for example, of a tumor associated with the medical condition. The digitized WSI can comprise a plurality of pixels, wherein each pixel can have an associated intensity.

The set of operations 200 can further comprise, at 220, analyzing (e.g., via a sliding window, etc.) the digitized WSI with an adversarially trained Fully Convolutional Network (e.g., as discussed herein) to determine the prognostic significance of each of the pixels of the digitized WSI.

The set of operations 200 can further comprise, at 230, generating a PS (Prognostic Significance) map of the digitized WSI that indicates an associated PS for each pixel of the digitized WSI. In some embodiments, a PS map can instead be generated having a lower resolution, such that each pixel of the PS map corresponds to a plurality of pixels of the WSI.

The set of operations 200 can further comprise, at 240, selecting the N tiles of the digitized WSI that have the highest total PS among tiles of the digitized WSI, as determined based on the PS map of the digitized WSI.

The set of operations 200 can further comprise, at 250, computing, for each tile of the N tiles, an associated prognostic metric for that tile based on the determination of one or more histomorphometric features for that tile. In various embodiments, the associated prognostic metric can be determined by a classifier (e.g., QDA, LDA (Linear Discriminant Analysis), SVM (Support Vector Machine), etc.) that has been trained to generate prognoses for the medical condition based on the one or more histomorphometric features. Additionally, in various embodiments, the one or more histomorphometric features can be handcrafted features that have been selected because of their high prognostic relevance for the medical condition.

The set of operations 200 can further comprise, at 260, generating a prognosis based on the associated prognostic metrics computed for each tile of the N tiles. The generated prognosis can comprise one or more of: a most likely prognostic outcome (e.g., as determined based on the histomorphometric features, etc.) such as recurrence, non-recurrence, etc., a probability or confidence associated with a most likely prognostic outcome; and/or associated probabilities/confidences associated with each of a plurality of prognostic outcomes.

Techniques and aspects of various embodiments are further explained below, in connection with an example embodiment that facilitates determination of a prognosis of recurrence or non-recurrence of early stage NSCLC.

Example Use Case: Predicting Recurrence/Non-Recurrence of Early Stage NSCLC

Figure 3:
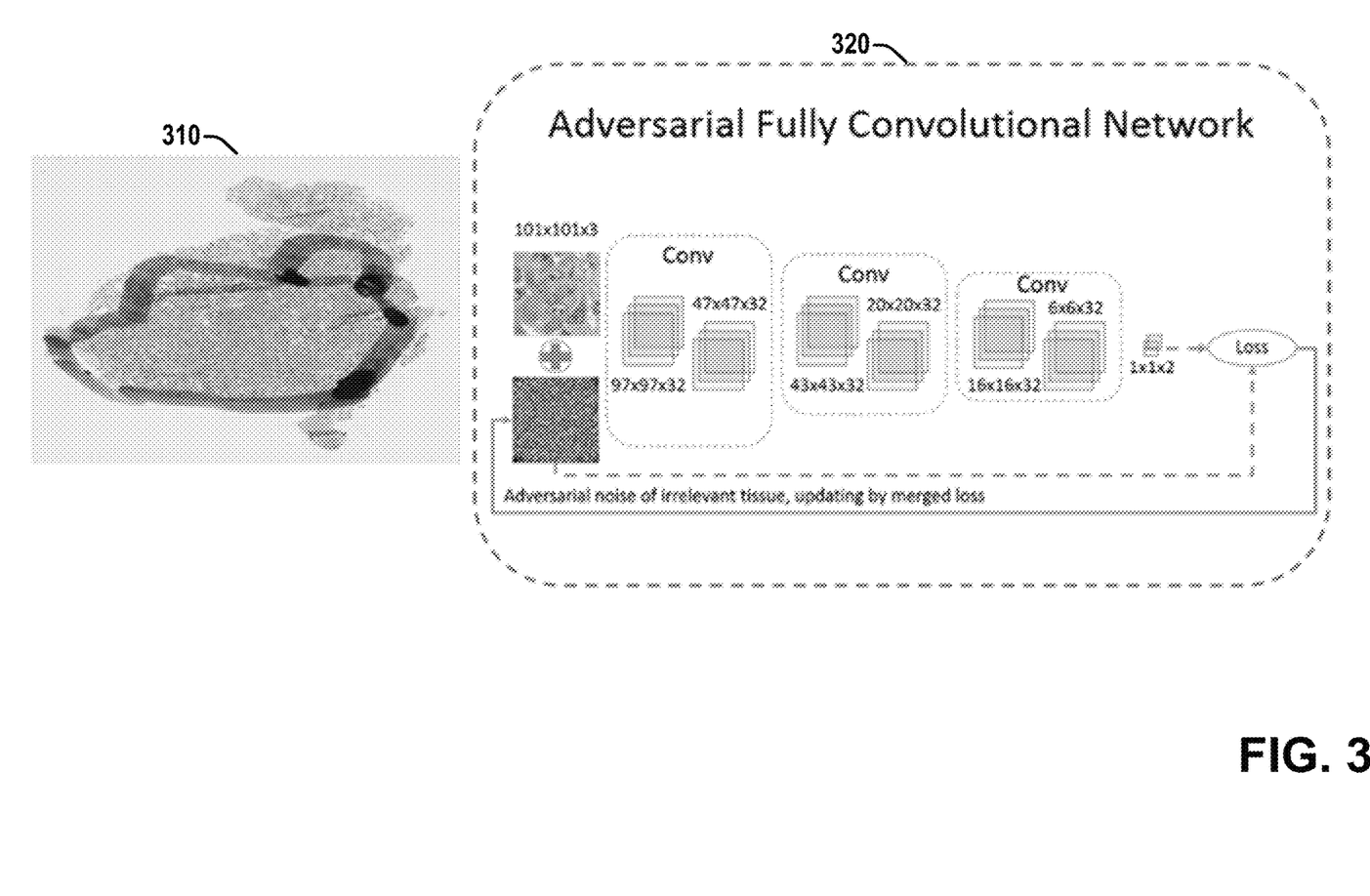
FIG. 3 illustrates a first pair of diagrams of examples of operations of sequential integration of adversarial networks with handcrafted features (SANwicH) techniques, according to various aspects discussed herein.
Figure 4:
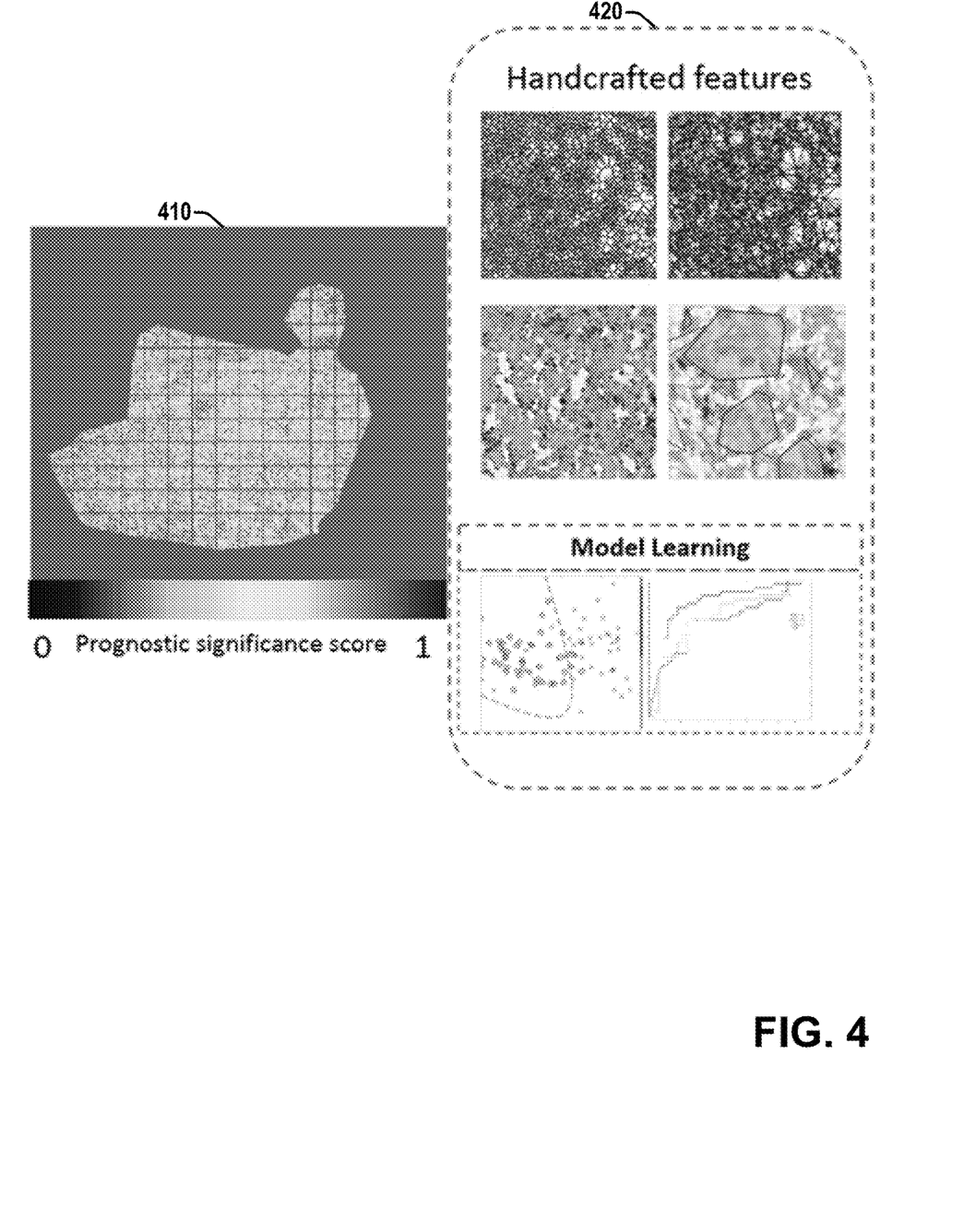
FIG. 4 illustrates a second pair of diagrams showing examples of operations of sequential integration of adversarial networks with handcrafted features (SANwicH) techniques, according to various aspects discussed herein.

Referring to FIG. 3, illustrated is a first pair of diagrams showing examples of the operations of sequential integration of adversarial networks with handcrafted features (SANwicH) techniques, according to various aspects discussed herein. Referring to FIG. 4, illustrated is a second pair of diagrams showing examples of the operations of sequential integration of adversarial networks with handcrafted features (SANwicH), according to various aspects discussed herein. FIGS. 3 and 4 show example images of an overall flow based on SANwicH techniques, according to an example embodiment for generating a prognosis of recurrence or non-recurrence in connection with early stage NSCLC. As shown in FIGS. 3 and 4, based on a training dataset (e.g., comprising TMAs) of positive and negative training samples, histology-specific noise is found by adversarial training, where a robust fully convolutional network (FCN) is trained (e.g., as shown at image 320 of FIG. 3) to locate the most prognostic regions (e.g., as shown in the prognostic significance map 410 based on example WSI 310). Biologically driven handcrafted features (e.g., as shown at image 420 of FIG. 4) are then applied to build a prediction model for recurrence risk in early stage NSCLC. Independent training and validation was employed to evaluate the approach. Additionally, the approach was also compared to a strategy involving random tile sampling from the WSI images.

Materials and Techniques

Data Description:

A first dataset (Dataset 1) comprising digitized TMAs from N=189 NSCLC patients from Site 1 was employed to train an embodiment configured to employ SANwicH techniques. A total of N=50 patient samples, whose recurrence have been correctly predicted by reported histomorphometric classifiers, were treated as positive training samples with the underlying assumption that those tissue regions contained the most relevant histomorphometric information pertaining to disease outcome. The negative training samples comprised another set of N=50 patients, these tissue samples comprised largely irrelevant or likely non-prognostic patterns including normal stromal tissue, tissue with artifacts (i.e. folding and missing), and non-diagnostic tissue (frozen tissue). A second dataset (Dataset 2) comprising whole slide images (WSIs) corresponding to surgically resected specimens from N=50 NSCLC patients was independently collected from Site 2. Dataset 2 was employed to validate whether the regions selected by SANwicH contained more accurate and consistent information for prognosis prediction when compared to approaches that employed averaging the signal from randomly selected tiles across the WSI. All WSIs and TMAs were digitally scanned at 20×, and informed patient consent was obtained in conjunction with appropriate IRB (Institutional Review Board) approval.

WSI Prediction via Fully Convolutional Network:

The fully convolutional neural network (FCN) employed in example embodiments discussed herein was generated by adapting an existing neural network into the FCN. The FCN can take as input an image of any size and can generate a corresponding probability map based on the image, with the same size through a densely forward inference. Given the varying sizes of tissue images from diverse institutions and protocols, this approach is more efficient and practical compared to the preprocessing (i.e. resizing) required for traditional deep learning tasks. Image 320 of FIG. 3 shows details of the FCN configuration of the example embodiment. Input started with a 101×101×3 patch (in various embodiments, other sizes can be employed), wherein the last layer was replaced with a convolution operation with the same kernel size as the output from the previous layer (in various embodiments, the number of layers can vary, e.g., based on a size of an initial input and a stride or sampling factor). This sequence of operations can then generate a machine-based binary prediction for the input image patch. Once the predictive model is locked down, the network can then take as input any image of any arbitrary size and generate the corresponding output via a filter rarefaction approach.

Adversarial Training to Increase Model Robustness:

Adversarial noise (which can be used to deceive state-of-art deep neural networks) was found and added during the training optimization process. Addition of the adversarial noise during training optimization can make the network immune to perturbations, thereby improving the consistency and robustness of the prediction model. The initial step of the approach involved first training a FCN using regular gradient descent to discriminate the tissue usefulness based on training data. Small random noise to maximize the probability of false prediction can be generated per equation (1):

$$\eta^* = \nabla_\eta J(\eta, x, y) \quad (1),$$

which is a loss function combined with cross entropy of FCN and $L_2$ loss of noise, given by equation (2):

$$J(\eta, x, y) = H_{f(x+\eta)}(y==1) + L_2(\eta) \quad (2)$$

In equation (2), H(•) is the cross entropy of the noisy input, and the label y is always set to 1 (tissue contains information). This step can be performed to ensure that the injected noise causes the absolutely irrelevant tissue to be identified as being prognostically useful. $L_2$ regularization of noise can make the noise as small as possible and hence does not alter the visual morphology of tissue.

During the adversarial optimization stage, image regions which are either too compromised by noise or tissue related artifacts (ripping, folding, no tissue) can be selected so that these regions can be identified as not being relevant for subsequent analysis by the FCN. Finally, the FCN can be further optimized by adversarial noise to improve network immunity.

Prognosis Prediction and Evaluation:

The adversarial network was sequentially integrated to finally predict the recurrence of early stage non-small cell lung cancer. First, the trained network was employed to scan through the entire region of WSI to generate a probability map of prognosis significance. Then a sliding window (e.g., 2000×2000 pixel in the example embodiment, although in various aspects, a window having a different size and/or shape (e.g., not square) can be employed) moved through the tissue region to pick up the top N tiles with the highest sum of value within the window. Finally, the previously reported histomorphometric features were extracted only from the selected tiles to predict the recurrence. The area under the curve (AUC) of the receiver operating characteristic (ROC) curve from the histomorphometric classifier was used as a final metric to evaluate the overall efficacy of embodiments employing SANwicH techniques.

Experimental Results

A total of 200 training patches (of size 101×101×3) from each patient (total 20,000 training patches) were randomly sampled to train the FCN with adversarial optimization. The deep learning model was trained with 200 epochs based on Tensorow library version 1.2.1 and single Nvidia TITAN X graphic card.

Figure 5:
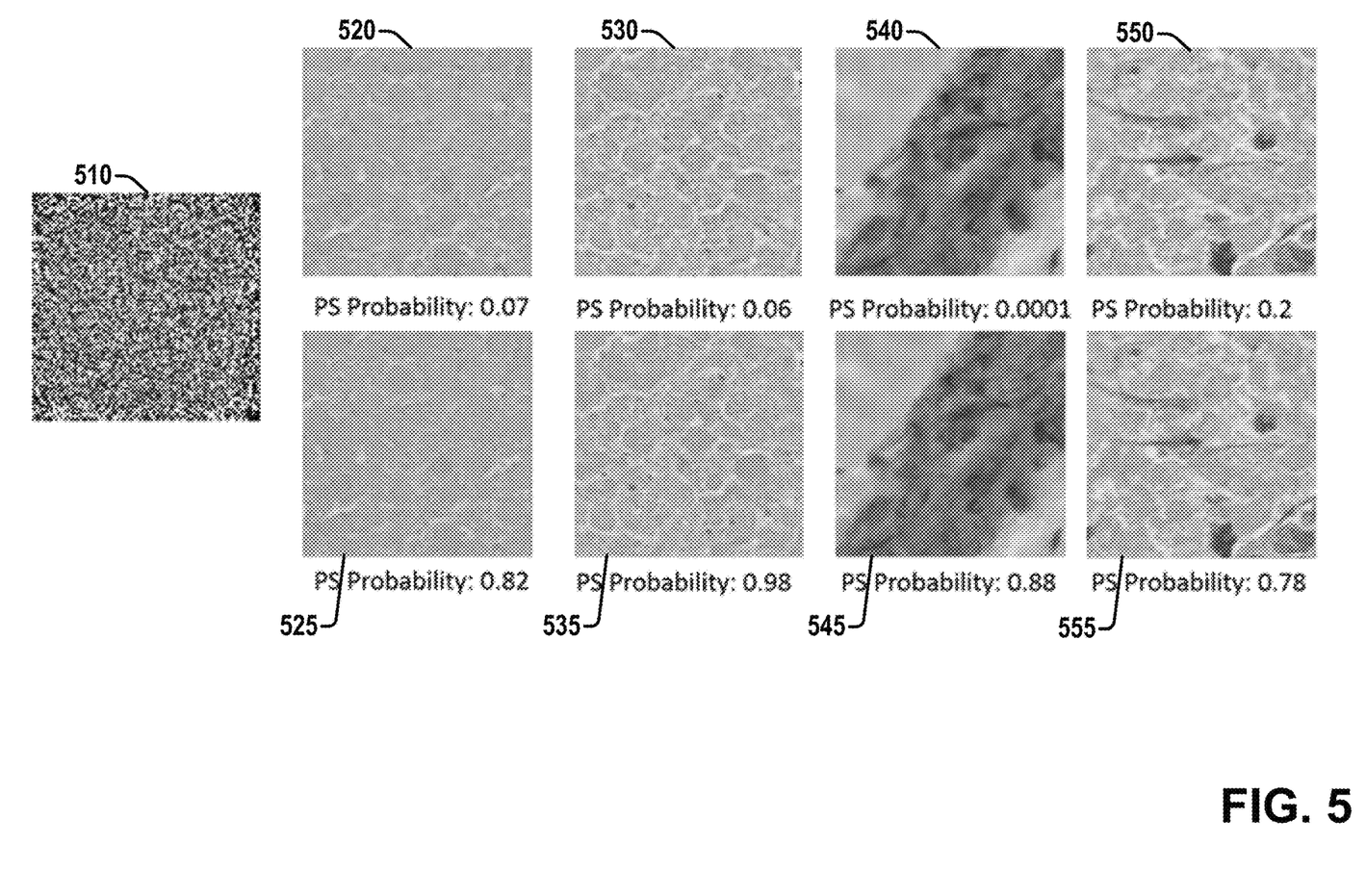
FIG. 5 illustrates a series of diagrams showing the weakness of a fully convolutional network (FCN) following the injection of adversarial noise, according to various aspects discussed herein.

A FCN network (learning rate 0.001 and 200 epoch) was first trained on dataset 1, with accuracy 0.92 on the validation set. Then adversarial noise was added to strengthen the network to account for variations in tissue appearance and artifacts. Referring to FIG. 5, illustrated is a series of diagrams showing the weakness of the network following the injection of adversarial noise, according to various aspects discussed herein. The top row of FIG. 5 shows the prognostic significance probability predicted for negative samples by the FCN (out of focus tissue at 520, tissue from a healthy person at 530, tissue folding at 540, and staining artifacts at 550). The addition of visually invisible adversarial noise greatly changes the prediction of PS probability of the same samples, as shown at 525, 535, 545, and 555. After adversarial training, the locked down FCN model was employed to perform a dense prediction of likelihood of recurrence on a pixel-by-pixel basis across the WSI. Based on this, a pixel wise prognostic significance (PS) map can be generated, such as the PS map shown at 410 in FIG. 4.

Each of three different tile sampling strategies were compared: (a) For SANwicH techniques, the top 5, 10, 15 and 20 1000×1000 PS tiles were evaluated (in various embodiments, other; (b) a random tile sampling strategy was evaluated, and (c) a strategy involving sampling all possible tiles in the WSI was evaluated.

To evaluate the utility of tiles selected by SANwicH techniques, the histomorphometric features (e.g. nuclear shape, texture) and quadratic discriminant analysis (QDA) were evaluated to compare the accuracy and robustness of final prediction of recurrence in early stage NSCLC. Area under curve (AUC) was determined for the following three different tile sampling approaches on dataset 2: (1) randomly selecting N tiles (for N ranging from 1-20); (2) selecting all tiles within the whole WSI; and (3) selecting the N tiles (for N ranging from 1-20) identified as the most prognostically relevant via SANwicH techniques.

Table 1, below, shows the final results in terms of AUC via each of these three different tile sampling approaches.

TABLE 1

Comparison of area under curve (AUC) of pre-built classifier for NSCLC recurrence risk between SANWicH, random sampling and all tiles for WSI on dataset 2

| Tile Number | SANwicH | Random | All |
|---|---|---|---|
| 5 | 0.8088 | 0.6899 | 0.6531 |
| 10 | 0.8125 | 0.7007 | |
| 15 | 0.8015 | 0.7062 | |
| 20 | 0.7923 | 0.7058 | |

Figure 6:
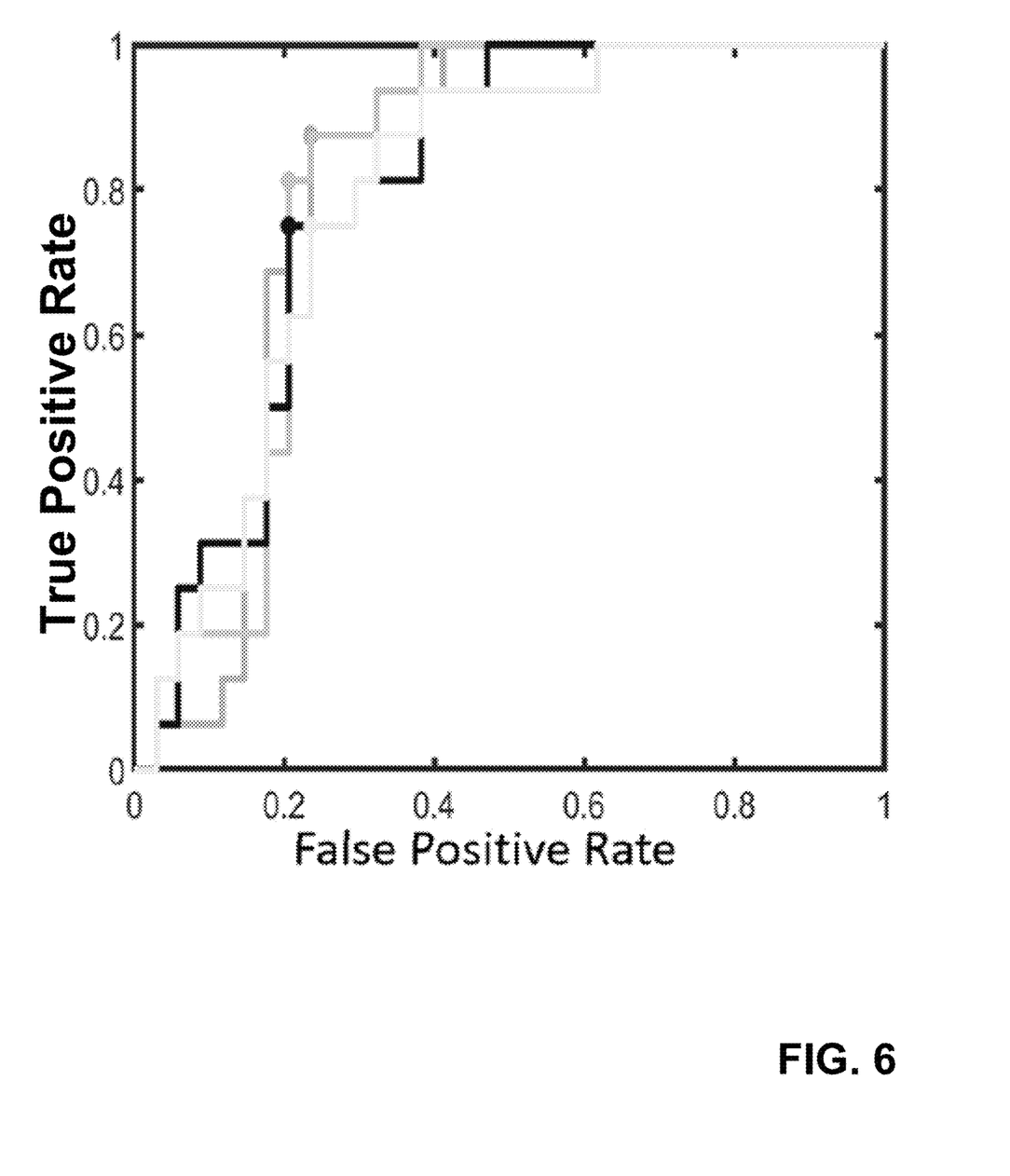
FIG. 6 illustrates a graph of receiver operating characteristic (ROC) curves for example embodiments employing SANwicH techniques sampling 5, 10, 15, and 20 tiles of a WSI (Whole Slide Image), according to various aspects discussed herein.
Figure 7:
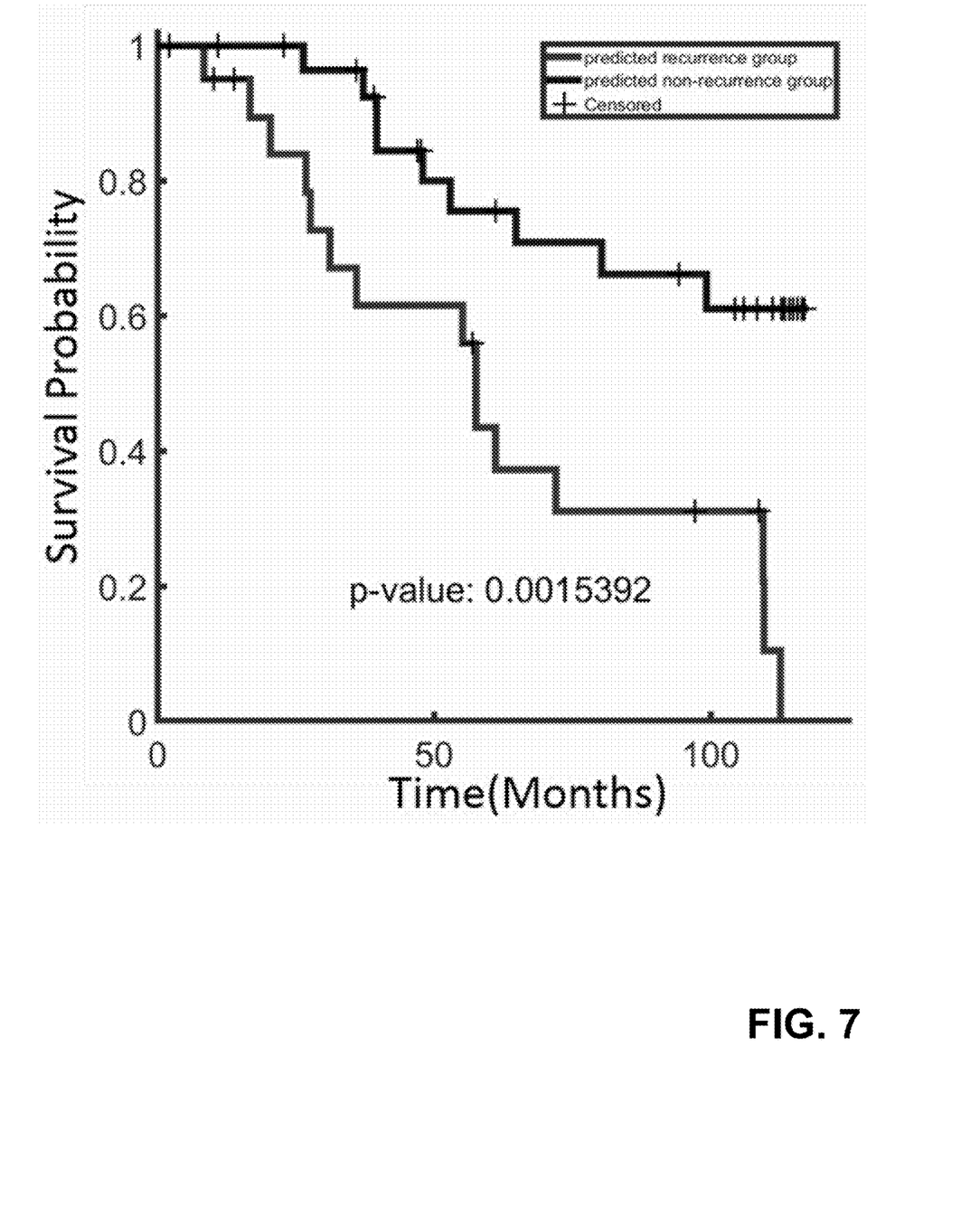
FIG. 7 illustrates a graph of Kaplan-Meier survival analysis for an example embodiment employing SANwicH techniques sampling 10 tiles of the WSI, according to various aspects discussed herein.

Referring to FIG. 6, illustrated is a graph of receiver operating characteristic (ROC) curves for example embodiments employing SANwicH techniques sampling 5, 10, 15, and 20 tiles of the WSI, according to various aspects discussed herein. Referring to FIG. 7, illustrated is a graph of Kaplan-Meier survival analysis for an example embodiment employing SANwicH techniques sampling 10 tiles of the WSI, according to various aspects discussed herein.

In terms of area under the ROC curve on the test set (dataset 2), embodiments employing SANwicH techniques resulted in the best performance across all of 5, 10, 15, and 20 tiles compared to the two other sampling strategies. Additionally, the SANwicH classifier (for each of the 5, 10, 15, and 20 tiles) resulted in statistically significant discrimination between patients with early versus late recurrence (p<0.0016). The classifiers obtained via the two other sampling strategies did not result in a statistically significant prognostic prediction on the test set.

Various embodiments can comprise and/or employ a fully convolutional network trained by adversarial pathological noise to select the most prognostically informative regions in whole slide image(s) (WSI(s)). Various embodiments can employ SANwicH techniques discussed herein, which, unlike existing techniques, can combine traditional handcrafted features with deep learning to identify sites of recurrence and/or predict disease outcome. Experimental results discussed herein indicate that embodiments employing SANwicH techniques are more stable and achieve higher accuracy when compared to other sampling strategies. In various embodiments, beyond a certain point, as the number of tiles increase, the prediction accuracy drops. This potentially implies that, owing to intra-tumoral heterogeneity, exhaustively extracting features from across the entire landscape of the tumor might actually be detrimental in predicting disease outcome. However, the number of tiles that maximizes AUC may vary between embodiments, for example, depending on the specific tissue and/or training dataset.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to sequential integration of adversarial networks with handcrafted features (SANwicH) facilitate determination of regions having high prognostic significance within a digitized WSI of tissue associated with a medical condition (and generation of an associated prognosis based on those regions) that are not perceivable by the human eye, and their computation cannot be practically performed in the human mind. A machine learning classifier as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then used and applied to create desired results more accurately, more consistently, and with greater reliability than existing approaches, thereby producing the technical effect of improving the performance of the machine, computer, or system with which embodiments are implemented.

Figure 8:
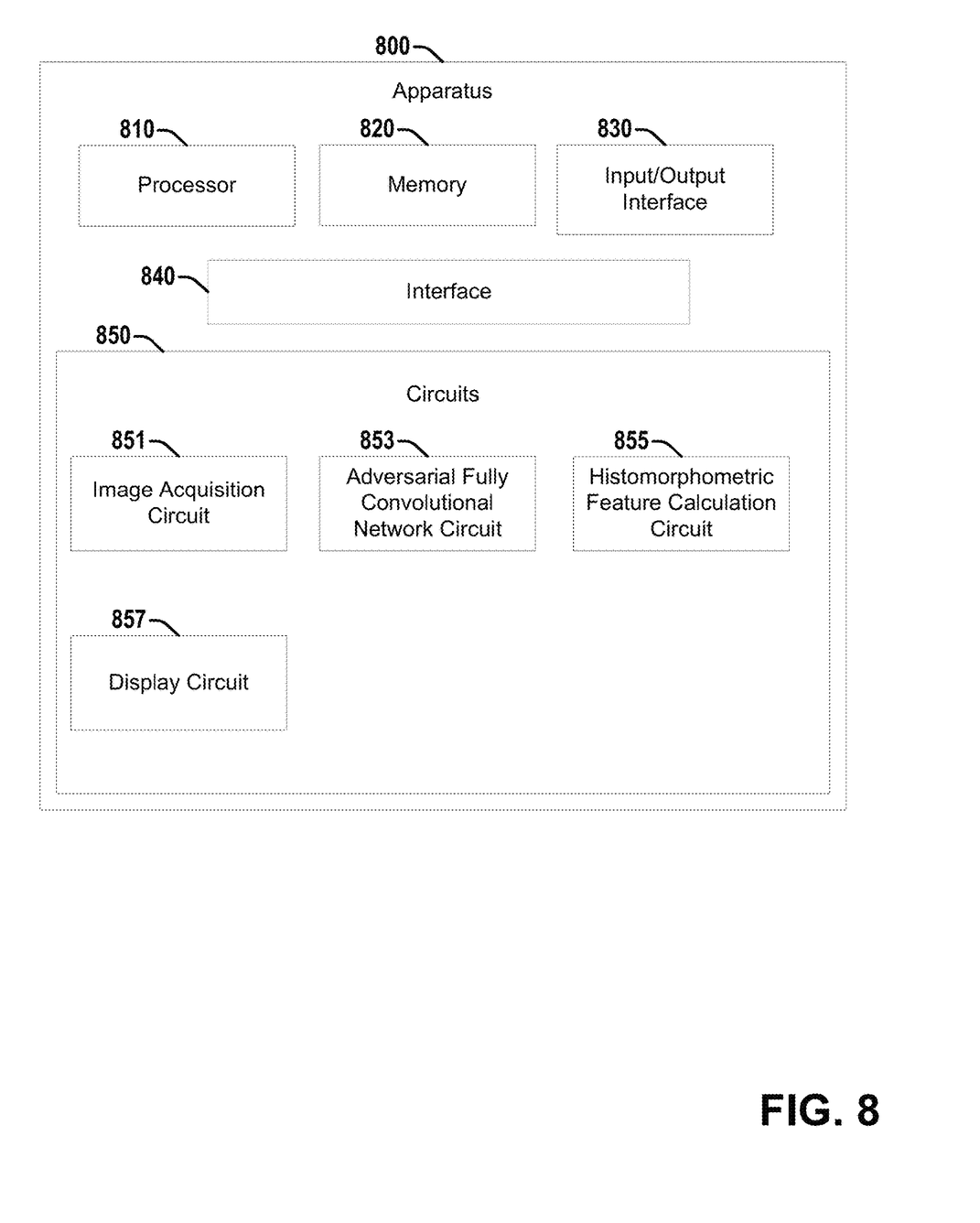
FIG. 8 illustrates a diagram of a first example apparatus that can facilitate training and/or employing sequential integration of adversarial networks with handcrafted features (SANwicH) according to various embodiments discussed herein.

Referring to FIG. 8, illustrated is a diagram of a first example apparatus 800 that can facilitate training and/or employing sequential integration of adversarial networks with handcrafted features (SANwicH) according to various embodiments discussed herein. Apparatus 800 can be configured to perform various techniques discussed herein, for example, training a fully convolutional network based on sequential integration of adversarial networks with handcrafted features (SANwicH) techniques discussed herein and/or employing such a FCN to generate a prognosis for a medical condition based on a WSI of tissue associated with the medical condition. Apparatus 800 comprises a processor 810. Apparatus 800 also comprises a memory 820. Processor 810 can, in various embodiments, comprise circuitry such as, but not limited to, one or more single-core or multi-core processors. Processor 810 can include any combination of general-purpose processors and dedicated processors (e.g., graphics processors, application processors, etc.). The processor(s) can be coupled with and/or can comprise memory (e.g. memory 820) or storage and can be configured to execute instructions stored in the memory 820 or storage to enable various apparatus, applications, or operating systems to perform operations and/or methods discussed herein. Memory 820 can be configured to store one or more digitized histological images (e.g., TMAs and/or WSIs). Each of the digitized histological image(s) can have a plurality of pixels, each pixel having an associated intensity. In some embodiments, memory 820 can store a training set of images (e.g., comprising TMAs) for training a FCN (Fully Convolutional Network) to determine prognostic significance of pixels of a WSI, while in the same or other embodiments, memory 820 can comprise a WSI to be evaluated by a trained FCN to determine regions of prognostic significance. Memory 820 can be further configured to store prognostic metric(s) computed for tile(s) of a WSI based on one or more histomorphometric features and/or a prognosis generated for a WSI based on one or more histomorphometric features.

Apparatus 800 also comprises an input/output (I/O) interface 830 (e.g., associated with one or more I/O devices), a set of circuits 850, and an interface 840 that connects the processor 810, the memory 820, the I/O interface 830, and the set of circuits 850. I/O interface 830 can be configured to transfer data between memory 820, processor 810, circuits 850, and external devices, for example, an optical microscope or scanner to obtain and/or scan histological images.

The set of circuits 850 can comprise an image acquisition circuit 851, an adversarial fully convolutional network circuit 853, a histomorphometric feature calculation circuit 855, and a display circuit 857, although some embodiments may omit one or more of these circuits (e.g., an embodiment that trains a FCN based on techniques discussed herein but does not apply the FCN to generate prognoses may omit histomorphometric feature calculation circuit 855). Image acquisition circuit 851 is configured to access one or more digitized histological images (e.g., a training set of TMAs and/or a WSI for which a prognosis is to be determined). Accessing the digitized histological image(s) can comprise accessing digitized histological image(s) stored in memory 820. In one embodiment, accessing the digitized histological image(s) can include accessing digitized histological image(s) stored in a data storage device, including a hard disk drive, a solid state device, a tape drive, or accessing digitized histological image(s) over a local area network. Accessing the digitized histological image(s) can comprise acquiring electronic data, reading from a computer file, receiving a computer file, reading from a computer memory, or other computerized activity not practically performed in the human mind.

In some embodiments, Adversarial Fully Convolutional Network Circuit 853 is configured to train a fully convolutional network on a training set of digitized histology images and adversarial noise to generate prognoses associated a medical condition based on a digitized WSI of tissue associated with the medical condition. In the same or other embodiments, Adversarial Fully Convolutional Network Circuit 853 is configured to generate prognoses associated a medical condition based on a digitized WSI of tissue associated with the medical condition. In various embodiments, Adversarial Fully Convolutional Network Circuit 853 can perform operations such as operations 110, 120, and 130 of set of operations 100 and/or operations 210, 220, 230 and 240 of set of operations 200.

Histomorphometric feature calculation circuit 855 can calculate one or more histomorphometric features (e.g., which can be handcrafted features selected for their high prognostic value in connection with a specific medical condition) for a region of a digitized histology image. In various embodiments, histomorphometric feature calculation circuit 855 can calculate the one or more histomorphometric features for each of N tiles of a WSI that have the highest prognostic significance as determined by adversarial fully convolutional network circuit 853. Based on the one or more histomorphometric features calculated for each tile of the N tiles, histomorphometric feature calculation circuit 855 can determine a prognostic metric for that tile. Based on the prognostic metrics for the N tiles, histomorphometric feature calculation circuit 855 can generate a prognosis for the medical condition. In various embodiments, histomorphometric feature calculation circuit 855 can employ a classifier (e.g., QDA) trained to determine prognoses for the medical condition based on the one or more histomorphometric features. In various embodiments, histomorphometric feature calculation circuit 855 can perform operations such as operations 250 and 260 of set of operations 200.

Display circuit 857 is configured to output or display the prognosis determined by histomorphometric feature calculation circuit 855. In various embodiments, the prognosis can comprise one or more of a most likely prognostic outcome (e.g., as determined based on the histomorphometric features, etc.) such as recurrence, non-recurrence, etc., a probability or confidence associated with a most likely prognostic outcome; and/or associated probabilities/confidences associated with each of a plurality of prognostic outcomes.

Figure 9:
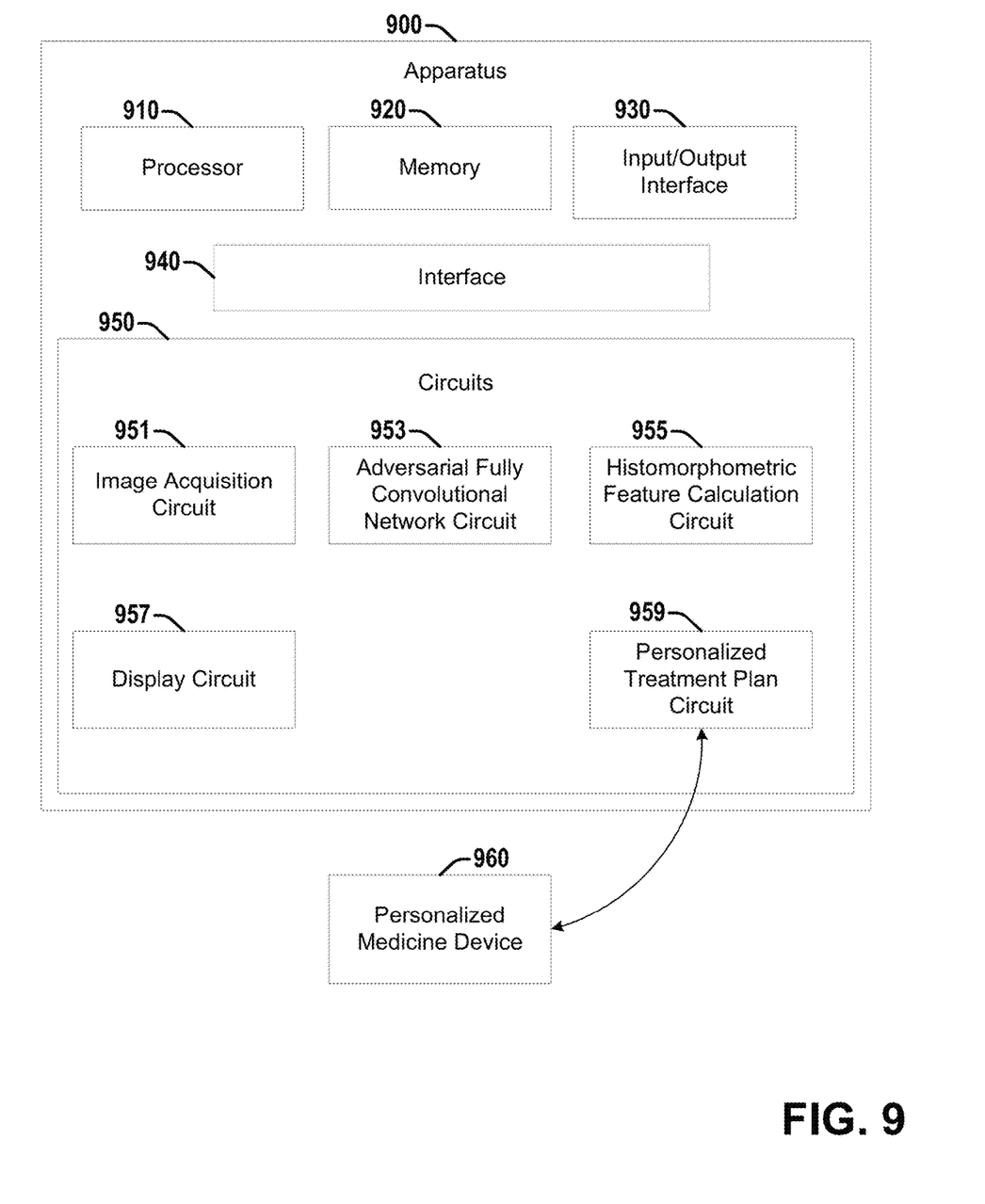
FIG. 9 illustrates a diagram of a second example apparatus that can facilitate training and/or employing sequential integration of adversarial networks with handcrafted features (SANwicH) according to various embodiments discussed herein.

Referring to FIG. 9, illustrated is a diagram of a second example apparatus 900 that can facilitate system-independent perfusion imaging according to various embodiments discussed herein. Example apparatus 900 is similar to the example apparatus of FIG. 8 (e.g., with elements 910-957 corresponding to elements 810-857, etc.), but comprises additional details and elements. Apparatus 900 can also comprise personalized treatment plan circuit 959. Personalized treatment plan circuit 959 can be configured to generate a personalized treatment plan based, at least in part, on a prognosis obtained from histomorphometric feature calculation circuit 955 or display circuit 957. Personalized treatment plan circuit 1059 can be configured to generate a personalized treatment plan for the patient of whom the WSI was acquired based, at least in part, on the prognosis derived therefrom. Defining a personalized treatment plan facilitates delivering a particular treatment that will be therapeutically active to the patient, while minimizing negative or adverse effects experienced by the patient. For example, the personalized treatment plan may suggest a surgical treatment, may suggest a pharmaceutical agent dosage or schedule, (e.g., for tumor-related embodiments) a chemotherapy agent dosage or schedule, and/or other treatments.

Apparatus 900 can further comprise personalized medicine device 960. Apparatus 900 can be configured to provide the prognosis, personalized treatment plan, or other data to personalized medicine device 960. Personalized medicine device 960 may be, for example, a computer assisted diagnosis (CADx) system or other type of personalized medicine device that can be used to facilitate the prediction of disease recurrence. In one embodiment, personalized treatment plan circuit 959 can control personalized medicine device 960 to display the prognosis, personalized treatment plan, or other data on a computer monitor, a smartphone display, a tablet display, or other displays.

Examples herein can include subject matter such as an apparatus, an optical microscopy system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: accessing a digitized whole slide image (WSI) of tissue associated with a medical condition, wherein the digitized WSI comprises a plurality of pixels, wherein each pixel of the plurality of pixels has an associated intensity; analyzing the digitized WSI with an adversarially trained fully convolutional network (FCN) to determine, for each pixel of the plurality of pixels, an associated prognostic significance (PS) for that pixel; generating a PS map corresponding to the digitized WSI that indicates, for each pixel of the plurality of pixels, the associated PS for that pixel; dividing the digitized WSI into a plurality of tiles, wherein each tile of the plurality of tiles is a square comprising an associated k×k pixels of the plurality of pixels, wherein each tile has a tile PS based on the associated PSs of each pixel of the associated k×k pixels of that tile; selecting N tiles of the plurality of tiles, wherein the selected N tiles have the N highest tile PS among tiles of the plurality of tiles; computing, for each of the N tiles, an associated prognostic metric for that tile based on one or more histomorphometric features; and generating a prognosis for the WSI in connection with the medical condition based on the associated prognostic metrics computed for each tile of the N tiles.

Example 2 comprises the subject matter of any variation of any of example(s) 1, wherein each histomorphometric feature of the one or more histomorphometric features comprise one or more handcrafted features selected for prognostic significance with respect to the medical condition via at least one of a minimum redundancy maximum relevance algorithm or quadratic discriminant analysis (QDA).

Example 3 comprises the subject matter of any variation of any of example(s) 1-2, wherein each histomorphometric feature of the one or more histomorphometric features is one of a global graph feature, a nuclear cluster graph feature, a nuclei shape feature, a nuclei orientation entropy feature, or a nuclei texture feature.

Example 4 comprises the subject matter of any variation of any of example(s) 1-3, wherein the medical condition is early stage non-small cell lung cancer (NSCLC).

Example 5 comprises the subject matter of any variation of any of example(s) 1-4, wherein N is less than or equal to 20.

Example 6 comprises the subject matter of any variation of any of example(s) 5, wherein N is 10.

Example 7 comprises the subject matter of any variation of any of example(s) 1-6, wherein k is 1000.

Example 8 comprises the subject matter of any variation of any of example(s) 1-7, wherein, for each pixel, the associated PS for that pixel is generated by the FCN via forward inference.

Example 9 comprises the subject matter of any variation of any of example(s) 1-8, wherein, for each pixel, the associated PS for that pixel is generated by the FCN based on a binary prediction for an input image patch around that pixel.

Example 10 comprises the subject matter of any variation of any of example(s) 1-9, wherein the prognosis is one of recurrence or non-recurrence.

Example 11 is an apparatus that facilitates generation of a prognosis in connection with a medical condition, the apparatus comprising: a processor; a memory configured to store a digitized whole slide image (WSI) of tissue associated with the medical condition, wherein the digitized WSI comprises a plurality of pixels, wherein each pixel of the plurality of pixels has an associated intensity; an input/output (I/O) interface; a set of circuits; and an interface that connects the processor, the memory, the I/O interface, and the set of circuits, the set of circuits comprising: an image acquisition circuit configured to access the digitized WSI; an adversarial fully convolutional network circuit configured to: analyze the digitized WSI to determine, for each pixel of the plurality of pixels, an associated prognostic significance (PS) for that pixel; generate a PS map corresponding to the digitized WSI that indicates, for each pixel of the plurality of pixels, the associated PS for that pixel; divide the digitized WSI into a plurality of tiles, wherein each tile of the plurality of tiles is a square comprising an associated k×k pixels of the plurality of pixels, wherein each tile has a tile PS based on the associated PSs of each pixel of the associated k×k pixels of that tile; and select N tiles of the plurality of tiles, wherein the selected N tiles have the N highest tile PS among tiles of the plurality of tiles; a histomorphometric feature calculation circuit configured to: compute, for each of the N tiles, an associated prognostic metric for that tile based on one or more histomorphometric features; and generate a prognosis for the WSI in connection with the medical condition based on the associated prognostic metrics computed for each tile of the N tiles; and a display circuit configured to output the prognosis for the WSI in connection with the medical condition.

Example 12 comprises the subject matter of any variation of any of example(s) 11, wherein each histomorphometric feature of the one or more histomorphometric features comprise one or more handcrafted features selected for prognostic significance with respect to the medical condition via at least one of a minimum redundancy maximum relevance algorithm or quadratic discriminant analysis (QDA).

Example 13 comprises the subject matter of any variation of any of example(s) 11-12, wherein each histomorphometric feature of the one or more histomorphometric features is one of a global graph feature, a nuclear cluster graph feature, a nuclei shape feature, a nuclei orientation entropy feature, or a nuclei texture feature.

Example 14 comprises the subject matter of any variation of any of example(s) 11-13, wherein the medical condition is early stage non-small cell lung cancer (NSCLC).

Example 15 comprises the subject matter of any variation of any of example(s) 11-14, wherein N is less than or equal to 20.

Example 16 comprises the subject matter of any variation of any of example(s) 15, wherein N is 10.

Example 17 comprises the subject matter of any variation of any of example(s) 11-16, wherein, for each pixel, the associated PS for that pixel is generated by the FCN via forward inference.

Example 18 comprises the subject matter of any variation of any of example(s) 11-17, wherein, for each pixel, the associated PS for that pixel is generated by the FCN based on a binary prediction for an input image patch around that pixel.

Example 19 is a non-transitory computer-readable medium storing computer-executable instructions that, when executed, cause a processor to perform operations, comprising: accessing a training dataset of digitized tissue microarrays (TMAs) comprising a positive set and a negative set, wherein each TMA of the positive set comprises one or more histomorphometric features that are predictive of an outcome of the medical condition, wherein each TMA of the negative set is non-prognostic, and wherein each digitized TMA of the training dataset comprises a plurality of associated pixels, wherein each pixel of the plurality of associated pixels of that digitized TMA has an associated intensity; training a fully convolutional network (FCN) based on the training dataset to produce a trained FCN; and further training the trained FCN based on adversarial noise to produce an adversarially trained FCN, wherein the adversarial noise is generated to maximize a probability of false prediction from the trained FCN.

Example 20 comprises the subject matter of any variation of any of example(s) 19, wherein the negative set comprises at least one TMA comprising at least one or more of normal stromal tissue, tissue with one or more artifacts, or non-diagnostic tissue.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2*d*. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
    accessing a digitized whole slide image (WSI) of tissue associated with a medical condition, wherein the digitized WSI comprises a plurality of pixels, wherein each pixel of the plurality of pixels has an associated intensity;
    analyzing the digitized WSI with an adversarially trained fully convolutional network (FCN) to determine, for each pixel of the plurality of pixels, an associated prognostic significance (PS) for that pixel;
    generating a PS map corresponding to the digitized WSI that indicates, for each pixel of the plurality of pixels, the associated PS for that pixel;
    dividing the digitized WSI into a plurality of tiles, wherein each tile of the plurality of tiles is a square comprising an associated k×k pixels of the plurality of pixels, wherein each tile has a tile PS based on the associated PS of each pixel of the associated k×k pixels of that tile;
    selecting N tiles of the plurality of tiles, wherein the selected N tiles have N highest tile PS among tiles of the plurality of tiles;
    computing, for each of the N tiles, an associated prognostic metric for that tile based on one or more histomorphometric features; and
    generating a prognosis for the digitized WSI in connection with the medical condition based on the associated prognostic metric computed for each tile of the N tiles.

2. The non-transitory computer-readable medium of claim 1, wherein each histomorphometric feature of the one or more histomorphometric features comprise one or more handcrafted features selected for prognostic significance with respect to the medical condition via at least one of a minimum redundancy maximum relevance algorithm or quadratic discriminant analysis (QDA).

3. The non-transitory computer-readable medium of claim 1, wherein each histomorphometric feature of the one or more histomorphometric features is one of a global graph feature, a nuclear cluster graph feature, a nuclei shape feature, a nuclei orientation entropy feature, or a nuclei texture feature.

4. The non-transitory computer-readable medium of claim 1, wherein the medical condition is early stage non-small cell lung cancer (NSCLC).

5. The non-transitory computer-readable medium of claim 1, wherein N is less than or equal to 20.

6. The non-transitory computer-readable medium of claim 5, wherein N is 10.

7. The non-transitory computer-readable medium of claim 1, wherein k is 1000.

8. The non-transitory computer-readable medium of claim 1, wherein, for each pixel, the associated PS for that pixel is generated by the FCN via forward inference.

9. The non-transitory computer-readable medium of claim 1, wherein, for each pixel, the associated PS for that pixel is generated by the FCN based on a binary prediction for an input image patch around that pixel.

10. The non-transitory computer-readable medium of claim 1, wherein the prognosis is one of recurrence or non-recurrence.

11. An apparatus that facilitates generation of a prognosis in connection with a medical condition, the apparatus comprising:
    a processor;
    a memory configured to store a digitized whole slide image (WSI) of tissue associated with the medical condition, wherein the digitized WSI comprises a plurality of pixels, wherein each pixel of the plurality of pixels has an associated intensity;
    an input/output (I/O) interface;
    a set of circuits; and
    an interface that connects the processor, the memory, the I/O interface, and the set of circuits, the set of circuits comprising:
        an image acquisition circuit configured to access the digitized WSI;
        an adversarial fully convolutional network circuit configured to:
            analyze the digitized WSI to determine, for each pixel of the plurality of pixels, an associated prognostic significance (PS) for that pixel;
            generate a PS map corresponding to the digitized WSI that indicates, for each pixel of the plurality of pixels, the associated PS for that pixel;
            divide the digitized WSI into a plurality of tiles, wherein each tile of the plurality of tiles is a square comprising an associated k×k pixels of the plurality of pixels, wherein each tile has a tile PS based on the associated PS of each pixel of the associated k×k pixels of that tile; and
            select N tiles of the plurality of tiles, wherein the selected N tiles have N highest tile PS among tiles of the plurality of tiles;
        a histomorphometric feature calculation circuit configured to:
            compute, for each of the N tiles, an associated prognostic metric for that tile based on one or more histomorphometric features; and
            generate the prognosis for the digitized WSI in connection with the medical condition based on the associated prognostic metric computed for each tile of the N tiles; and
        a display circuit configured to output the prognosis for the digitized WSI in connection with the medical condition.

12. The apparatus of claim 11, wherein each histomorphometric feature of the one or more histomorphometric features comprise one or more handcrafted features selected for prognostic significance with respect to the medical condition via at least one of a minimum redundancy maximum relevance algorithm or quadratic discriminant analysis (QDA).

13. The apparatus of claim 11, wherein each histomorphometric feature of the one or more histomorphometric features is one of a global graph feature, a nuclear cluster graph feature, a nuclei shape feature, a nuclei orientation entropy feature, or a nuclei texture feature.

14. The apparatus of claim 11, wherein the medical condition is early stage non-small cell lung cancer (NSCLC).

15. The apparatus of claim 11, wherein N is less than or equal to 20.

16. The apparatus of claim 15, wherein N is 10.

17. The apparatus of claim 11, wherein, for each pixel, the associated PS for that pixel is generated by an adversarially trained fully convolutional network (FCN) via forward inference.

18. The apparatus of claim 11, wherein, for each pixel, the associated PS for that pixel is generated by an adversarially trained fully convolutional network (FCN) based on a binary prediction for an input image patch around that pixel.

\* \* \* \* \*